United States Patent [19]
Zeitels et al.

[11] Patent Number: 5,746,770
[45] Date of Patent: May 5, 1998

[54] ENDOSCOPIC RETRIEVER

[76] Inventors: Jerrold Roy Zeitels, 4 Ellsworth Dr., Warren, N.J. 07059; David Douglas Grewe, 3450 W. 83rd Ave., Westminister, Colo. 80030

[21] Appl. No.: 535,888

[22] Filed: Nov. 22, 1995

[51] Int. Cl.[6] .................................................. A61B 17/28
[52] U.S. Cl. ........................ 606/207; 600/223; 600/160; 600/182
[58] Field of Search .................... 606/205–210, 606/15, 16; 600/199, 200, 212, 223, 241, 245, 104, 160, 164, 166, 170, 171, 178, 182; 362/119, 120

[56] References Cited

U.S. PATENT DOCUMENTS

| | | |
|---|---|---|
| 4,027,510 | 6/1977 | Hiltebrandt . |
| 4,266,547 | 5/1981 | Komiya .................................. 606/15 |
| 4,633,870 | 1/1987 | Sauer ..................................... 606/16 |
| 4,753,235 | 6/1988 | Hasson ................................... 606/207 |
| 4,759,349 | 7/1988 | Betz et al. . |
| 4,972,828 | 11/1990 | Ito . |
| 5,020,514 | 6/1991 | Heckele . |
| 5,217,460 | 6/1993 | Knoepfler ............................... 606/205 |
| 5,242,439 | 9/1993 | Larsen et al. ........................... 606/15 |
| 5,290,279 | 3/1994 | Bonati et al. .......................... 606/15 |
| 5,304,203 | 4/1994 | El-Mallawany et al. ............... 606/205 |
| 5,456,684 | 10/1995 | Schmidt et al. ....................... 606/207 |

FOREIGN PATENT DOCUMENTS

| | | |
|---|---|---|
| 5337073 | 6/1992 | Japan . |
| 2151142 | 11/1984 | United Kingdom . |

*Primary Examiner*—Michael Buiz
*Assistant Examiner*—Patrick W. Rasche
*Attorney, Agent, or Firm*—Jonathan E. Grant

[57] ABSTRACT

An endoscopic retriever comprising an endoscope and retriever is disclosed, wherein the illuminating light passes at right angles to the plane of the grasping jaws of the retriever. In one embodiment of the invention, at least one illuminating light guide fiber travels partly through at least one of the grasping arms and passes perpendicular to the length of at least one of the grasping jaws through at least one of the grasping laws, terminating in at least one of the two jaws at right angles to the plane of the jaw. The endoscope may have a torque handle to control the grasping force of the jaws of the retriever.

19 Claims, 3 Drawing Sheets

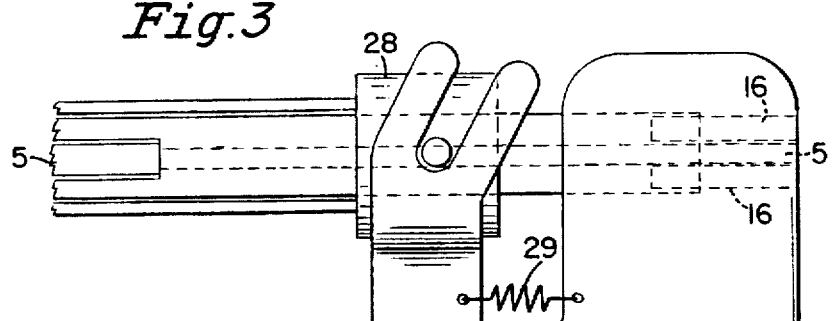
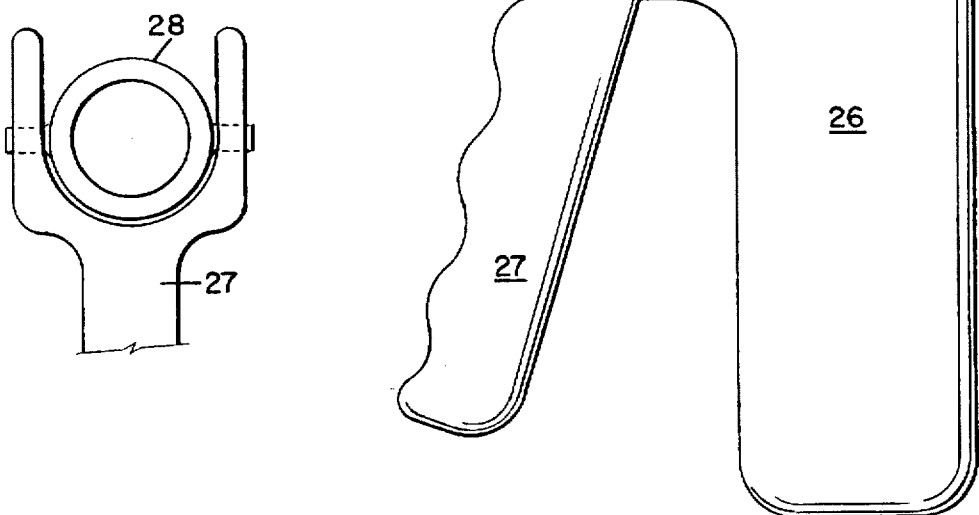
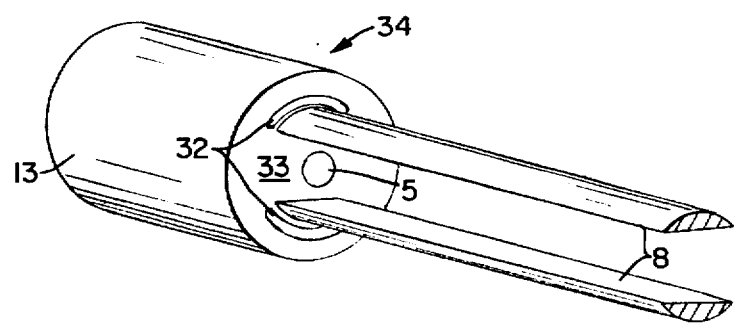
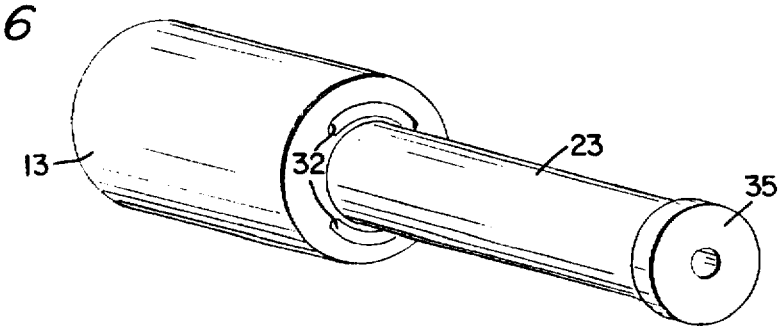

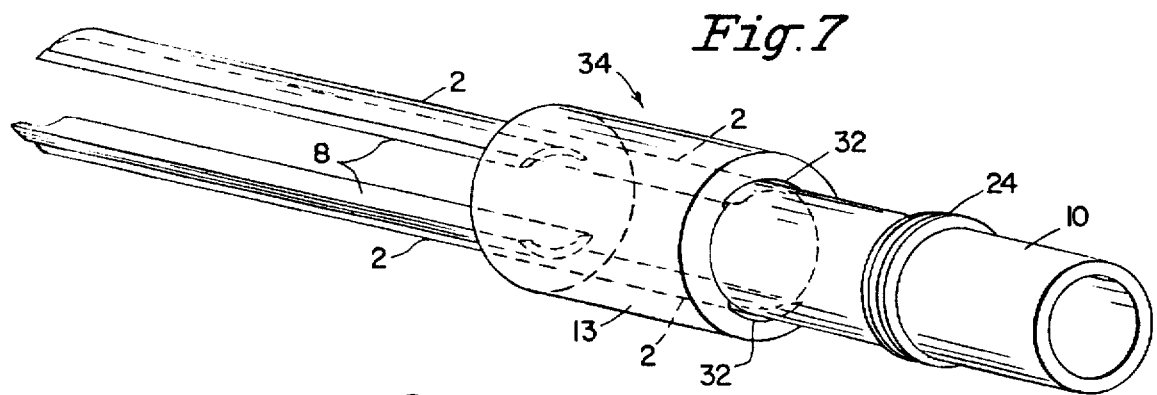
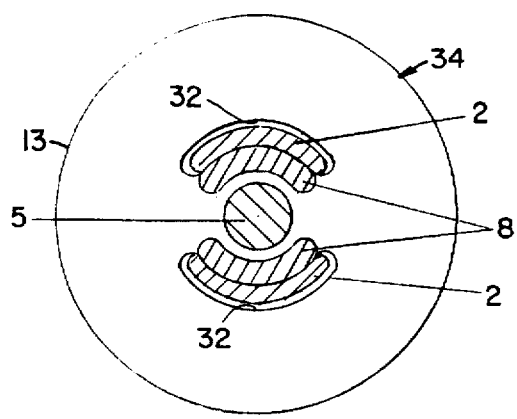
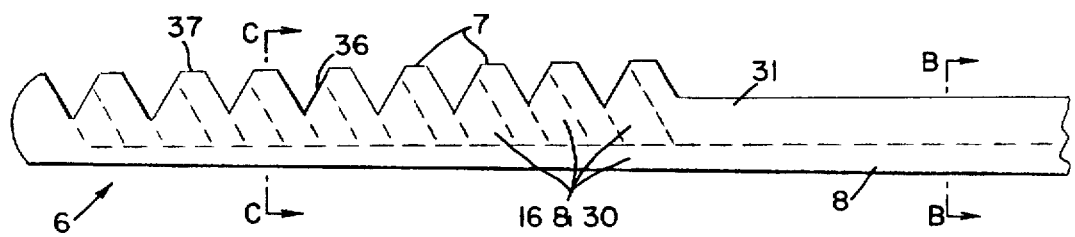
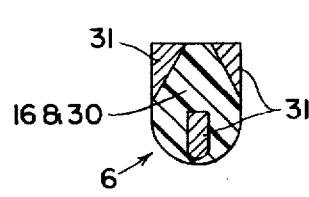
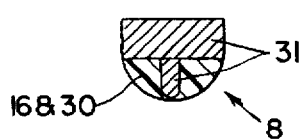

ENDOSCOPIC RETRIEVER

BACKGROUND OF THE INVENTION

1. Field of the Invention

The present invention discloses an endoscopic retriever.

2. Description of the Prior Art

Over the years, there have been many surgical devices developed wherein arthroscopes or endoscopes were combined with cutters, forceps, or other manipulative surgical instruments in order to improve the ability of the surgeon to visualize the area of the body in which he was operating.

JP-A 5-337073 (Taguchi) discloses a pair of grip forceps having an insertion section and a grip section provided at its tip. An operation section for opening or closing the grip member is provided at the base end of the insertion section. A guide light fiber probe, the end of which appears above the grip forceps, is connected to a laser beam source device via a fiber connector.

U.S. Pat. No. 4,027,510 (Hiltebrandt) discloses a forceps instrument having a viewing splint extending centrally through the barrel which is longitudinally movable to open and close the forceps jaws; the view splint terminates in a straight line, giving the surgeon an uninterrupted view between the forceps jaws. When the handle is squeezed, the barrel moves in the distal direction in relation to the optical system, slides over the jaws forming the mouth and thus closes the pair of jaws and the clip.

U.S. Pat. No. 4,972,828 (Ito) discloses an endoscope having a connecting portion extending between an operating portion and an insertion portion which is sheathed with a cylindrical casing having a forceps insertion inlet projecting therefrom.

U.S. Pat. No. 5,020,514 (Heckele) discloses an endoscope for nasal surgery comprising an outer shaft having a handle incorporating a switching valve for connecting a suction and flushing channel of the outer shaft to, and disconnecting it from, a source of negative pressure and a source of flushing fluid.

Patent No. GB 2,151 142A (Bonnet) discloses an endoscope having a passage through which passes a shaft of an auxiliary instrument such as a probe, forceps or bundle of glass fibers. The instrument shaft has an angled distal end portion projecting from the passage and includes at least a resiliently flexible angled portion.

U.S. Pat. No. 5,290,279 (Bonati et al) discloses a multi-function arthroscope having a laser channel, an irrigation splint, a suction splint, a rod lens, and optical fibers housed within a tubular casing. The operation site is illuminated by the optical fibers. The physician views the illuminated site through the rod lens, performs laser surgery with laser radiation propagated by the laser channel, irrigates the site and cleans the rod lens with saline solution through the irrigation splint, and vacuums the debris with the suction splint, all in a single insertion of the arthroscope through a "dilator" splint.

U.S. Pat. No. 4,759,349 (Betz et al.) discloses a surgical instrument having a heat sink for irrigation, aspiration and illumination. Specifically, the endoscope comprises a surgical instrument and a support unit for enabling a user, using one hand, to probe an incision and illuminate, irrigate, and aspirate the incision. The surgical instrument has a probe with illumination, irrigation, and aspiration ports on the end. The probe is coupled to a handle having controls for the irrigation and aspiration functions.

All of these inventions lack the ability to illuminate and visualize the exact area of the body in which the surgical procedure is occurring. More specifically, in the inventions described above, the light of the endoscope is emitted at a point distant from the site of the surgery where the actual manipulation of the body is taking place such that illumination of the area being operated on is limited.

SUMMARY OF THE INVENTION

The present invention proposes a surgical device allowing for improved illumination and manipulation of the site of surgery. More specifically, the present invention discloses an endoscopic retriever comprising an endoscope and a retriever. The retriever has a pair of opposing grasping arms, which comprise a pair of grasping jaws. Illuminating light passes at right angles to the plane of said grasping jaws. This may be accomplished by at least one of two ways. In one embodiment of the invention, light guide fibers are positioned in the retriever to provide cross-illumination or intratissue illumination. The light conduit fibers terminate in at least one of two jaws at right angles to the plane of the jaw. This effects a cross-illumination of the end of the tendon which results in shadowing on the tendon end and, hence, better depth perception. Furthermore, when the tendon end is grasped in a way such that the fiber ends directly contact the tendon, light will pass from the fibers into the tendon.

In another embodiment of the invention, the grasping arms are comprised of light conducting plastic, except for the teeth of the jaws which are uncoated, thereby allowing light to exit from the teeth.

In yet another embodiment of the invention, the grasping arms could be a combination of metal and light-conductive glass or plastic with the glass or plastic being in the form of fibers. The endoscopic retriever, exclusive of the endoscope, may be entirely comprised of plastic.

In yet another embodiment of the invention, the teeth of the jaws of the retriever are spaced and rounded to provide maximum grasping force and minimal trauma to the end of a tendon, nerve, or other body part being grasped.

The endoscopic retriever may also include an irrigating channel which can be incorporated into the instrument to rinse any areas of blood or non-transparent material obfuscating the view of the surgeon.

In one embodiment of the invention, the endoscopic retriever is operated by means of a spring loaded scissors grip.

In another embodiment of the invention, the endoscopic retriever is operated by means of a movable torque handle, which, when rotated, advances splints longitudinally along the length of the grasping arms, therein closing the grasping jaws around the body part to be grasped. The endoscope of the retriever is positioned between and set back from the grasping arms.

In yet another embodiment of the invention, the splints and the grasping arms are resilient and flexible so as to allow the retriever to conform to the actual shape of the tendon sheath. The splints and the grasping arms may be constructed of a material selected from the group consisting of thin walled stainless steel, an Austenitic nickel-titanium tubing, and closely wound steel spring wire.

In yet another embodiment of the invention, the splints and the grasping arms are formable, enabling the retriever to be formed into a curvature. In this embodiment, the splints and grasping arms may be constructed of a soft steel or Martensitic crystal form of nickel-titanium.

The distal end of the endoscopic retriever may also have an elliptical cross section and the entire retriever may be less than one centimeter in diameter, for ease of use during surgery so as to avoid further traumatization of the area of surgery.

BRIEF DESCRIPTION OF THE DRAWINGS

The above and other objects, features and advantages of the present invention will become more readily apparent from the following description, reference being made to the accompanying drawings in which:

FIG. 3 is a longitudinal view of another embodiment of the present invention;

FIG. 4 is a partial cross-sectional view of another embodiment of the invention;

FIG. 5 is an angular view of the distal and middle sections of the grasping arms of one embodiment of the endoscopic retriever;

FIG. 6 is an angular view of the middle and proximal section of the grasping arms of one embodiment of the endoscopic retriever;

FIG. 7 is an angular cutaway view of the the grasping arms and of the splints;

FIG. 8 is a frontal cross-sectional view of one embodiment of the invention;

FIG. 9 is an enlarged side view of the jaws of the grasping arm;

FIG. 10 is an enlarged cross sectional view of the distal end of the grasping arm;

FIG. 11 is an enlarged cross sectional view of the grasping jaws; and

DESCRIPTION OF THE PREFERRED EMBODIMENT

Figure 1:
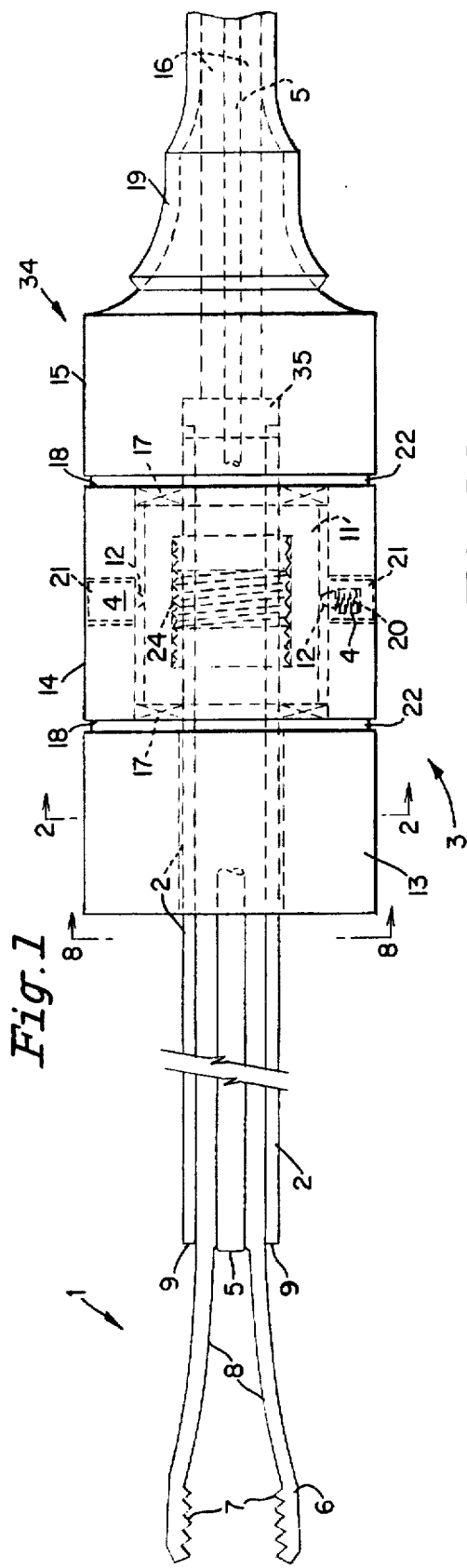
FIG. 1 is a longitudinal partial cross-sectional view of one embodiment of the present invention.
Figure 12:
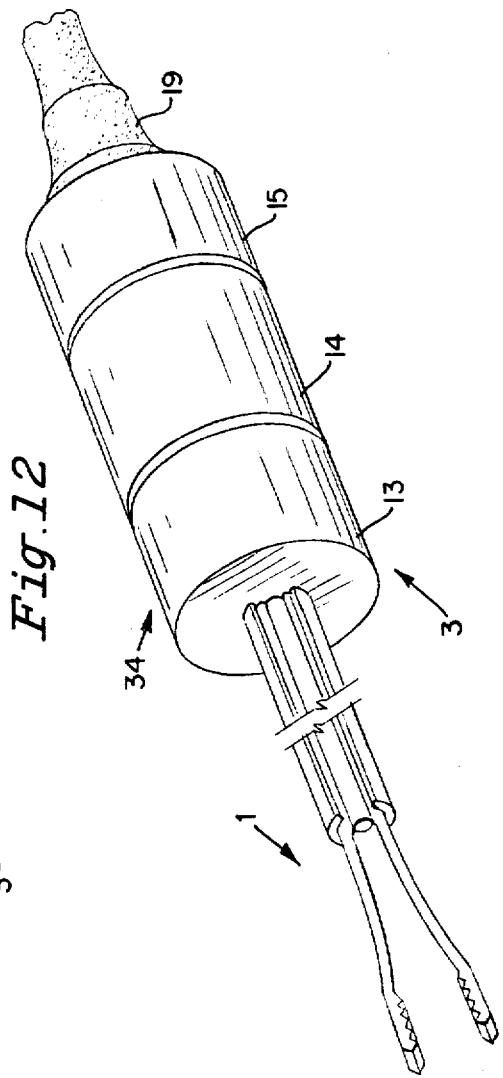
FIG. 12 is an angular view of the endoscopic retriever.
Figure 2:
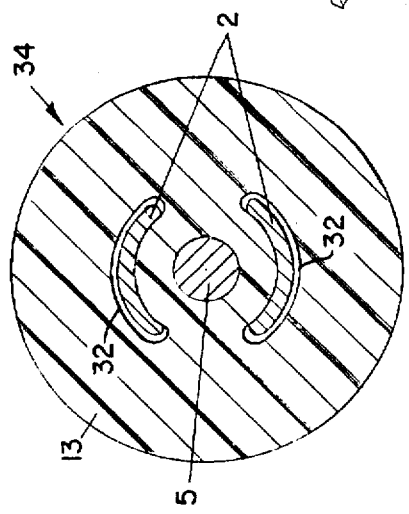
FIG. 2 is a cross-sectional view of the distal handle section of one embodiment of the present invention.

Referring to FIGS. 1–12, the endoscopic retriever 1 comprises a pair of opposing grasping arms 8 at the distal end of a grasping tool 34, with grasping jaws 6 positioned at the distal end of the opposing grasping arms 8. The grasping jaws 6 have opposing teeth 7 which are spaced and rounded to provide maximum grasping force and minimal trauma to the end of a tendon, nerve or other body part being grasped. The teeth 7 are arranged in a staggered fashion such that the teeth of the top jaw fit between the teeth of the bottom jaw. In another embodiment of the invention, the grasping jaws may be in the form of forceps. The teeth of the grasping jaws may also be roughened.

To illuminate the areas of the body being operated on, it is preferred that illuminating light pass at an angle between about 45 degrees to about 90 degrees to the plane of grasping jaws 6, with light preferably passing at a 45 degree angle or right angle to the plane of the grasping jaws 6. This may be accomplished by at least one of two ways. At least one illuminating light guide fiber 16 travels partly through one of the grasping arms 8 and angularly to the length of the grasping jaw 6 at the end of the grasping arm 8, terminating preferably at a 45°–90° angle to the plane of the jaw 6. In another version of the invention, an illuminating light guide fiber 16 travels through each of the grasping arms 8 and each fiber 16 passes perpendicular to the length of one grasping jaw 6 terminating at 45°–90° angles to the plane of the jaw 6, such that each of the two grasping jaws 6 has an illuminating light guide fiber 16 terminating angularly to the plane of the jaw 6. The light guide fiber(s) 16 may be affixed to the wall of the grasping arm and jaw by any conventional means, including but not limited to the use of a glue, an epoxy resin 30 or a bracketing arrangement. Preferably, the optical fibers are secured to the metal 31 with epoxy resin 30. In other embodiments of the invention the light fiber may pass through at least one jaw at angles outside of the 45°–90° range.

In another embodiment of the invention as shown in FIGS. 9–11, the grasping arms 6 are comprised of light conducting plastic, except for the teeth 7 of the jaws which are uncoated, to allow light to exit from them.

In yet another embodiment of the invention, the grasping arms 8 of the grasping tool 34 could be a combination of metal and light-conductive glass or plastic with the glass or plastic being in the form of fibers. In the embodiments of the invention where light conducting plastic is used, the illuminating fibers 16 may terminate where the light conducting plastic of the grasping arms begins.

Illumination fibers 16 may run through the proximal end of proximal handle section 15 up through the handle and into the proximal ends of the grasping arms 6.

Two forms of illumination are provided to illuminate the tendon or body part being operated on. Light originating at the endoscope 5 reflects off the tendon-end-surface and into the endoscope imaging optics. Additionally, light which enters the tendon from the teeth 7 when the tendon is grasped transilluminates the tendon. Some of this light will also enter the endoscope imaging optics 5. These combined types of illumination will enhance the operator's ability to obtain the optimum grip on the tendon end.

The endoscopic retriever further comprises an endoscope 5 positioned between the proximal ends of the grasping arms 8 and throught the center of the entire grasping tool 34. While other endoscopes of the appropriate shape and size may be used, the preferred endoscope 5 is a Mitsubishi Model TAS 201/1.0 which has a small outer diameter, is highly flexible and is comprised of imaging and illumination fiber optic bundles and optics. To visualize the surgical site, the proximal ends of the endoscope imaging bundle connects to a TV camera (not shown) for image display on a TV monitor.

To operate the retriever so that the grasping jaws 6 close around the tendon, splints 2 are positioned longitudinally around the grasping arms 8, with the endoscope positioned between grasping arms 8 and through the grasping tool 34. The distal ends 9 of the splints 2 are rounded to prevent soft tissue damage when the retriever is in use during surgery and to prevent gouging of the grasping arm.

The splints 2 may be comprised of steel or memory metal such as a nickel-titanium alloy with an Austenitic crystal structure for flexible properties. Alternatively, the metal splints 2 may be comprised of alloys of a soft steel or of nickel-titanium with a Martinistic crystal structure to permit shaping the distal end in a curve which is similar to the tendon shaft curvature.

The proximal end 10 of the splints are threaded to interact with a floating ring 11. Longitudinal grooves are present in the floating ring 11 to interact with balls 12 in the ball screws 4, which are positioned in handle 3.

FIGS. 5–7 show the relationship between the splints 2 and the grasping tool 34. In a preferred embodiment of the invention, the grasping tool 34 consists of several sections. At the distal end of the grasping arms 8 are the grasping jaws 6 and opposing teeth 8, shown in FIGS. 1 and 9–11. The arms 8 extend into the distal handle section 13 of the grasping tool 34. The distal handle 13 contains slots 32 for the splint(s) 2 to pass through to surround the grasping arms 8. The proximal section 23 of the grasping tool 34 passes through the middle rotatable handle section 14 and through the proximal handle section 15. The surface portion 35 of the proximal end 23 of the grasping tool 34 is then preferably attached to an elastomeric boot 19.

The splints 2 comprise a distal end 9 which surrounds the grasping arms 8 and passes through the distal slots 32 for the splints 2 in the distal and proximal sections of the distal handle sections of the grasping tool 34. The splints 2, after passing through distal handle section 13, preferably forms a circular proximal section 10. The proximal section 10 comprises a threaded portion 24 which is used in conjunction with the rotation of a middle rotatable handle section 14 to advance the splints along the length of the grasping arms 8 to close the grasping jaws 6.

The handle 3, which may be made of metal or plastic, surrounds the proximal ends of splints 2, the grasping arms 8, and the endoscope 5. The handle 3 is divided into three sections; a distal handle section 13 which is preferably part of the grasping tool 34, a middle rotatable handle section 14, and a proximal handle section 15. Preferably, washers or snap rings 22 are positioned between the proximal handle section 15 and the middle rotatable handle section 14, and between the middle rotatable handle section 14 and the distal handle section 13. It is preferred that the thin washers be made of high density polyethylene or tetrafluoroethylene. Illumination fiber optic bundles and optics 16 run through the back or bottom 17 of the proximal handle section 15. The proximal handle section 15 preferably has attached to it an elastomer boot 19 to hold the endoscope 5 and the optical fiber illumination bundles 16 in place. The fiber illumination bundles 16 abutt the proximal end of the grasping arms 8. It is preferred that the upper fiber illumination bundles not be used when the arms are metal, but that both bundles be used with the plastic version of the arms. The proximal end of the grasping arms 8 is adhesively bonded to the elastomer boot with an adhesive bond.

The middle rotatable handle section 14 is rotatable about the metal splints 2 and the grasping arms 8 near the proximal end 10 of the splints. At least two bearings 17, preferably sleeve bearings, positioned at the both ends 18 of the middle rotatable handle section 14, permit the middle rotatable handle section 14 to rotate freely around the splints 2 and the floating ring 11. The middle rotatable handle section 14 is in communication with the floating ring 11 by means of ball screws 4. At least two ball screws 4, and preferably three or four ball screws, are positioned on opposite sides of the middle rotatable handle and are in communication with the floating ring 11. The ball screws 4 each consist of a metal or plastic ball 12 above which is a helical spring 20. The compression of the spring is controlled by a set screw 21 located at the other end of the spring 20. In another embodiment of the invention a knob set screw may be used in place of set screws. These would permit adjustment of the spring tension, and, hence, the torque of the handle 3 by the device operator, which, in turn, determines the grasping force of the jaw teeth 7 on a tendon. In the preferred embodiment of the invention, the ball screw spring 20 compression will be factory adjusted to cause the handle 3 to slip when sufficient mechanical resistance is met as occurs when the grasping jaws 6 are grasping a tendon with a prescribed force. The distal end of the splints 2 will meet with increasing mechanical resistance as it advances and develops the grasping force.

It should be noted that the entire endoscopic retriever may be less than one centimeter in diameter. Additionally, while some versions of the device may be made primarily of metal, preferably steel, nickel-titanium alloys, etc., the device may be made almost entirely of plastic (exclusive of the endoscope) and be disposable.

This device is designed especially for use in tendon surgery. To use the device to grasp a tendon or other body part, the surgeon, after opening up the section of the body being operated on, grasps the distal handle section 13 and, with his right hand, rotates the middle rotatable handle section 14. When the middle rotatable handle 14 is rotated, the ball screw 4 rotates with the handle 3. As the ball screw 4 rotates to the left or right, depending on the tool's design, the floating ring 11 rotates with the ball screw 4. As the floating ring 11 rotates, the inner part of the floating ring, which is threaded and in communication with the proximal end 10 of the splints 2, causes the splints 2 to forwardly advance, causing the splints 2 to advance forwardly along the length of the grasping arms 8. Consequently, as the middle rotatable handle 14 of the torque handle 3 is rotated, the grasping arms 8 close around the tendon or other body part being operated. However, when the grasping arms 8 closes about the tendon, the resistance of the tendon to the grasping arms 8 is "felt" by the floating ring 11, and the ball screw 4 will start slipping, thereby preventing damage to the tendon.

It should be noted that the entire endoscopic retriever 1, exclusive of the endoscope 5, may be comprised of plastic.

In another embodiment of the invention, a scissor grip mechanism is used to cause the grasping jaws 6 to close. Referring to FIGS. 3 and 4, the endoscopic retriever 25 comprises a grip 26 attached to a trigger handle 27. A spring 29 is positioned between a grip and the trigger handle to cause the release of the grasping jaws 6 when the grip is released. When the trigger handle 27 is squeezed, a ring 28 encompassing the splints 2 is advanced distally against the splints 2, causing the splints to advance. As with the other embodiment of this invention, this results in closure of the grasping jaws 6 located at the distal end of the grasping arms 8. The two illumination bundles (the illumination fibers 16) plug into the proximal end of the grasping arms 8. The endoscope 5 passes along the center axis of the center axis of the grasping arms 8. More specifically, the endoscope is positioned between the grasping arms 8, exiting distally. The proximal ends of the grasping arms 8 and the grip 27 fit securely together. The proximal ends of the grasping arms 8 are attached in the grip 26 by any conventional means, including glue, screws, nuts and bolts, or any other means.

The principal application of the device described above is as a flexor tendon retriever. Its uniqueness is derived from the fact that the tendons can be visualized and grasped with as little trauma to the tendons as possible. Consequently, the amount of scarring and incisions that might otherwise be produced during this type of surgery should be greatly reduced.

This device could also be used in other fields of medicine. For instance, the device could be used to remove nasal polyps, which reside in the back recesses of the nose. The device could also be useful in endoscopic forehead lifts whereby through one or two incisions the corrugator muscles could be visualized, grasped and removed. Further, it could have applications in exploration of small joints of the hand, foot and other types of orthopedic surgery. It could visualize damaged tissue and remove unwanted debris. Besides its use in orthopedic surgery and possibly otolaryngology, the device may have uses in other medical fields.

Many modifications and variations of the present invention are possible in light of the above teachings. It is, therefore, to be understood within the scope of the appended claims the invention may be protected otherwise than as specifically described.

What is claimed is:

1. An endoscopic retriever comprising:
   an endoscope;
   a retriever, said retriever having a pair of opposing grasping arms, said grasping arms comprising a pair of grasping jaws, said grasping arms being positioned around an endoscope;
   at least one illuminating light guide fiber, said at least one light guide fiber travelling at least partly through at least one of said grasping arms, said at least one guide fiber passing perpendicular to a length of at least one of said grasping jaws through at least one of said grasping jaws, terminating in at least one of said grasping jaws at right angles to the plane of one of said grasping jaws;
   a handle, said handle having at least three sections, said three sections being a distal handle section which is integral with said grasping arms, a middle rotatable handle section, and a proximal handle section;
   distal slots positioned in said distal handle section;
   at least two splints, a distal end of said at least two splints surrounding a distal end of said grasping arms, and said at least two splints after passing through said distal slots positioned in said distal handle section having a common threaded circular proximal section, said middle rotatable handle section further comprising means to advance the splints along a length of the grasping arms to reversibly close the grasping jaws as said middle rotatable handle rotates about a longitudinal axis of said at least two splints, said means of said middle rotatable handle section being in communication with said common threaded circular proximal section of said at least two splints to reversibly advance said splints along said length of said graspings arms:
   and wherein said endoscope is positioned between said grasping arms, such that illuminating light passes angularly from a plane of at least one of said grasping jaws.

2. The endoscopic retriever of claim 1, wherein the grasping arms are comprised of light conducting plastic, except for an inner surface of each of said jaws which is uncoated, to allow light to exit said jaws.

3. The endoscopic retriever of claim 1, wherein an outer surface of each of said grasping arms is coated with a metal.

4. The endoscopic retriever of claim 1, wherein said grasping jaws further comprise a plurality of teeth, said teeth being positioned on an inner surface of said grasping jaws, said teeth being positioned on each said grasping jaw, said teeth of each said jaw being positioned opposite to each other, said teeth being spaced and rounded to provide maximum grasping force and minimal trauma to the end of a tendon, nerve, or other body part being grasped.

5. The endoscopic retriever of claim 4, wherein the teeth of said jaws are roughened.

6. The endoscopic retriever of claim 1, further comprising an irrigating channel incorporated into the endoscopic retriever.

7. The endoscopic retriever of claim 1, wherein said endoscope is positioned between and set back from said grasping arms.

8. The endoscopic retriever of claim 1, further comprising:
   a torque handle to control the grasping force of the jaws of the retriever, said torque handle being the middle rotatable handle section, and
   a floating ring, said middle rotatable handle section being in communication with said floating ring, said floating ring having a threaded inner part, wherein when the middle rotatable handle section is rotated, the floating ring rotates, and the inner part of the rotating floating ring, in communication with the threaded proximal end of the splints, causes the splints to reversibly forwardly advance, along the length of the grasping arms, causing the grasping arms to reversibly close around a body part upon which an operation is being conducted.

9. The endoscopic retriever of claim 8, wherein said splints are resilient and flexible, thereby allowing said retriever to conform to the actual shape of the tendon sheath.

10. The endoscopic retriever of claim 9, wherein said splints are constructed of a material selected from the group consisting of thin walled stainless steel, an Austenitic nickel-titanium tubing, and closely wound steel spring wire.

11. The endoscopic retriever of claim 9, wherein said retriever has an elliptical cross section.

12. The endoscopic retriever of claim 8, wherein said splints are formable, enabling the retriever to be bent to form a curvature.

13. The endoscopic retriever of claim 12, wherein said splints are constructed of a Martensitic crystal form of nickel-titanium.

14. The endoscopic retriever of claim 1, wherein the endoscopic retriever, exclusive of the endoscope, is comprised of plastic.

15. The endoscopic retriever of claim 1, wherein the entire retriever is less than one centimeter in diameter.

16. The endoscopic retriever of claim 1, wherein said retriever is in the form of a forceps.

17. The endoscopic retriever of claim 8, wherein said torque handle further comprises at least one ball screw, positioned in the middle rotatable handle section and in communication with said floating ring, wherein when the middle rotatable handle is rotated, the at least one said ball screw rotates with the handle, the floating ring rotates with the ball screw, the inner part of the floating ring, in communication with the threaded proximal end of the splints, causes the splints to reversibly forwardly advance, causing the splints to advance forwardly along the length of the grasping arms, causing the grasping arms to reversibly close around a body part upon which an operation is being conducted.

18. An endoscopic retriever, comprising:
   an endoscope;
   a retriever, said retriever having a pair of opposing grasping arms, said grasping arms comprising a pair of grasping jaws, said grasping arms being positioned around an endoscope;
   at least one illuminating light guide fiber, said at least one light guide fiber travelling at least partly through at least one of said grasping arms, said at least one guide fiber passing perpendicular to a length of at least one of said grasping jaws through at least one of said grasping jaws, terminating in at least one of said grasping jaws at right angles to the plane of at least one of said grasping jaws; and
   a scissor grip mechanism to cause said grasping jaws to close, said scissor grip mechanism comprising:
   a grip;
   a trigger handle, said grip attached to said trigger handle;
   a resilient member positioned between the grip and the trigger handle causing the release of the grasping jaws when the grip is released; at least two splints, wherein a distal end of said at least two splints surrounds a distal end of said grasping arms; and a ring encompassing the splints, said ring positioned near the proximal end of said splints, said ring positioned in a clevis near the top of the grip, forming a clevis lever, wherein when said grip is squeezed, said ring is advanced distally against the splints, causing the splints to advance, resulting in closure of said grasping jaws located at the distal end of said grasping arms.

19. An endoscopic retriever comprising:

an endoscope;

a retriever, said retriever having a pair of opposing grasping arms, said grassing arms comprising a pair of grasping jaws, said grasping arms being positioned around an endoscope;

a handle, said handle having at least three sections, said three sections being a distal handle section which is integral with said grasping arms, a middle rotatable handle section, and a proximal handle section, said endoscope positioned between said pair of opposing grasping arms;

distal slots positioned in said distal handle section;

at least two splints, a distal end of said at least two splints surrounding a distal end of said grasping arms, said at least two splints having a common threaded circular proximal section after passing through said distal slots positioned in said distal handle section said at least two splints;

a torque handle to control the grasping force of the jaws of the retriever, said torque handle being the middle rotatable handle section, said torque handle comprising at least one ball screw positioned in said middle rotatable handle section; and a floating ring, said floating ring having a threaded inner part said middle rotatable handle section being in communcation with said floating ring, such that said at least one ball screw interacts with said floating ring, wherein when the middle rotatable handle section is rotated, the ball screw rotates with the middle rotatable handle section, the floating ring rotates with the ball screw, the inner part of the rotating floating ring, in communication with the threaded proximal end of the splints, causes the splints to reversibly forwardly advance along the length of the grasping arms, causing the grasping arms to reversibly close around a body part upon which an operation is being conducted.

* * * * *